United States Patent
Curtis et al.

[11] Patent Number: 6,083,516
[45] Date of Patent: Jul. 4, 2000

[54] WEAR RESISTANT COSMETICS

[75] Inventors: Ernest S. Curtis, Milford, Pa.; Arvind N. Shah, Suffern, N.Y.; Harold E. Pahlck, Waldwick, N.J.

[73] Assignee: Avon Products, Inc., New York, N.Y.

[21] Appl. No.: 09/162,052

[22] Filed: Sep. 28, 1998

Related U.S. Application Data

[63] Continuation of application No. 08/824,510, Mar. 26, 1997, abandoned.

[51] Int. Cl.⁷ .................. A61K 7/025; A61K 17/032; A61K 7/031
[52] U.S. Cl. .................. 424/401; 424/63; 424/64; 424/69; 424/70.7; 424/78.02; 424/78.17; 424/78.18; 424/DIG. 5
[58] Field of Search .................. 424/401, 64, 63, 424/78.02, 70.7, 69, 78.17, 78.18, DIG. 5

[56] References Cited

U.S. PATENT DOCUMENTS

| | | |
|---|---|---|
| 3,925,241 | 12/1975 | Schmolka . |
| 3,928,558 | 12/1975 | Chessman et al. . |
| 4,032,628 | 6/1977 | Papantoniou et al. . |
| 4,336,246 | 6/1982 | Leon-Pekarek . |
| 4,411,887 | 10/1983 | Siebert et al. . |
| 4,719,099 | 1/1988 | Grollier et al. . |
| 4,767,613 | 8/1988 | Nuber et al. . |
| 4,798,721 | 1/1989 | Yahagi et al. . |
| 4,867,972 | 9/1989 | Girardeau et al. . |
| 4,883,659 | 11/1989 | Goodman et al. . |
| 4,960,814 | 10/1990 | Wu et al. . |
| 4,985,239 | 1/1991 | Yahagi et al. . |
| 5,000,946 | 3/1991 | Bird et al. . |
| 5,025,004 | 6/1991 | Wu et al. . |
| 5,061,481 | 10/1991 | Suzuki et al. . |
| 5,063,057 | 11/1991 | Spellman et al. . |
| 5,100,658 | 3/1992 | Bolich, Jr. et al. . |
| 5,104,642 | 4/1992 | Wells et al. . |
| 5,104,646 | 4/1992 | Bolich, Jr. et al. . |
| 5,106,609 | 4/1992 | Bolich, Jr. et al. . |
| 5,106,611 | 4/1992 | Forestier et al. . |
| 5,128,123 | 7/1992 | Brewster et al. . |
| 5,143,723 | 9/1992 | Calvo et al. . |
| 5,152,991 | 10/1992 | Vogel et al. . |
| 5,183,403 | 2/1993 | Masuhara et al. . |
| 5,208,038 | 5/1993 | Gressani et al. . |
| 5,219,560 | 6/1993 | Suzuki et al. . |
| 5,270,054 | 12/1993 | Bertolini . |
| 5,324,506 | 6/1994 | Calvo et al. . |
| 5,380,520 | 1/1995 | Dobbs . |
| 5,385,730 | 1/1995 | Ichinohe . |
| 5,413,775 | 5/1995 | Hatfield et al. . |
| 5,558,872 | 9/1996 | Jones et al. . |
| 5,565,194 | 10/1996 | Burkhart et al. . |
| 5,567,428 | 10/1996 | Hughes . |

*Primary Examiner*—Jyothsna Venkat
*Attorney, Agent, or Firm*—Ohlandt, Greeley, Ruggiero & Perle, LLP

[57] ABSTRACT

A wear-resistant cosmetic composition including a styrene-ethylene/propylene mixed block copolymer, preferably from about 0.1 weight percent to about 15 weight percent, in a cosmetically acceptable carrier. The cosmetic composition may also include an alkyl cycloalkylacrylate copolymer, preferably from about 0.1 weight percent to about 15 weight percent.

18 Claims, No Drawings

WEAR RESISTANT COSMETICS

This is a continuation, of application Ser. No. 08/824,510, filed Mar. 26, 1997 now abandoned.

The present invention relates generally to wear resistant cosmetic compositions. More particularly, this invention relates to a cosmetic composition containing a styrene-ethylene/propylene mixed block copolymer that demonstrates enhanced wear in combination with a smooth, non-tacky feel.

BACKGROUND OF THE INVENTION

Various organic waxes and film formers are known in the art for their ability to impart uniform films and protective barriers to the skin and lips. Most of these films are slow to dry on application. Because these films remain wet for extended periods of time, they adhere poorly and tend to transfer off the surface to which they are applied. This results in poor overall cosmetic wear, and requires that the user reapply the cosmetic frequently.

Those film formers that provide somewhat more rapid drying times have additional limitations. The primary limitation of these film formers is an unpleasant tacky feel on application to the skin, lips or lashes that is disliked by consumers. Also, these products tend to drag against the skin when applied, and leave the skin feeling dry and sticky.

Accordingly, there is a need for a wear-resistant cosmetic that forms a protective film on the skin that is also quick to dry and easy to apply, but does not have an unpleasant, undesirable tacky feel on the skin.

SUMMARY OF THE INVENTION

Against the foregoing background, it is a primary object of the present invention to provide a cosmetic composition having enhanced wear resistance.

It is another object of the present invention to provide a cosmetic composition that produces a quick drying protective film on the skin.

It is yet another object of the present invention to provide a wear resistant cosmetic composition that is not tacky and neither drags against the skin upon application nor dries the skin.

To the accomplishment of the foregoing objects and advantages, the present invention, in brief summary, comprises a wear-resistant cosmetic composition including a styrene-ethylene/propylene mixed block copolymer, preferably at from about 0.01 weight percent to about 85 weight percent, in a cosmetically acceptable carrier. The cosmetic composition may also include an alkyl cycloalkylacrylate copolymer, preferably at from about 0.01 weight percent to about 85 weight percent.

DESCRIPTION OF THE PREFERRED EMBODIMENTS

The present invention provides a wear-resistant cosmetic such as, for example, a lipstick, foundation, eye shadow, blush or mascara. It has surprisingly been found that a styrene-ethylene/propylene mixed block copolymer provides superior wear resistance to such cosmetic compositions or formulas, both alone and preferably in combination with an alkyl cycloalkylacrylate copolymer. Moreover, it has surprisingly been found that cosmetic formulas containing the styrene-ethylene/propylene mixed block copolymer are non-tacky and have a pleasant feel when applied to the skin. These compositions are easy to apply, have improved skin and lip adherence (transfer resistance), and provide enhanced wear and longevity.

Most preferably, the wear-resistant cosmetic composition according to the present invention includes a styrene-ethylene/propylene mixed block copolymer in a cosmetically acceptable carrier. This cosmetic composition may also include an alkyl cycloalkylacrylate copolymer as a primary ingredient or in combination with the mixed-block copolymer.

The preferred styrene-ethylene/propylene mixed block copolymer of the present invention is a block copolymer made up of styrene, ethylene and propylene type monomers having the following general structure:

Styrene

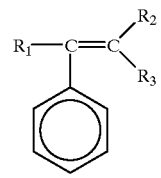

Ethylene

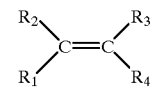

Propylene

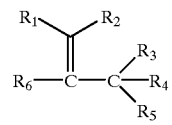

where $R_1$ to $R_6$ are independently hydrophobic alkyl chains. One possible structure of the copolymer, with the repeating monomer subset shown in brackets, is:

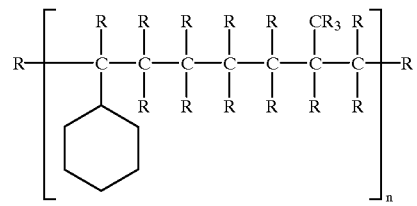

wherein $n \geq 1$ and the R groups may be the same or different, and are independently hydrophobic alkyl chains.

The most preferred styrene-ethylene/propylene mixed block copolymer for use in the present invention is available from Brooks Industries as Gel Base (Code 05895). Gel Base (Code 05895) is a styrene-ethylene/propylene mixed block copolymer in combination with isododecane, that is provided as a cloudy white gel. The specific structure of the Gel Base (Code 05895) styrene-ethylene/propylene mixed block copolymer is proprietary to Brooks Industries.

The Material Data Safety Sheet and product Specification Sheet for this Gel Base issued in March of 1996 states that it has an INCI Proposed Name of Isododecane and Styrene-Ethylene/Propylene Block Copolymer. It further states that the product has a white color, a boiling point of 178 to 183° C., a vapor pressure of 186 mbar @20° C., a vapor density of 5.9 (air-1), 0.5% maximum volatility by volume, a characteristic odor, and is insoluble in water.

This mixed block copolymer is not water soluble, but is soluble in certain oils and hydrocarbon solvents such as isoparaffin and isododecane. This allows the mixed block copolymer to be delivered in a volatile solvent base to the skin. Once delivered, the volatile solvent evaporates, at least partially, leaving the water insoluble mixed block copolymer film on the skin. This film resists transfer and wear. The mixed block copolymer is most preferably used in combination with a silicone-containing base (containing, for example, dimethicone/cyclomethicone) or an organic volatile in an aqueous base, for superior feel and wear.

In a preferred embodiment, the styrene-ethylene/propylene mixed block copolymer is from about 0.01 percent by weight to about 85 percent by weight (weight percent) of the total weight of the composition. In the most preferred embodiment, the styrene-ethylene/propylene mixed block copolymer is from about 0.1 to about 15 percent by weight of the composition. It should be understood that one or more styrene-ethylene/propylene mixed block copolymers may be used in the present compositions.

When the composition includes the alkyl-cycloalkylacrylate copolymer, the preferred alkyl cycloalkylacrylate copolymer is a copolymer or copolymers having the following formulas and the isomers thereof:

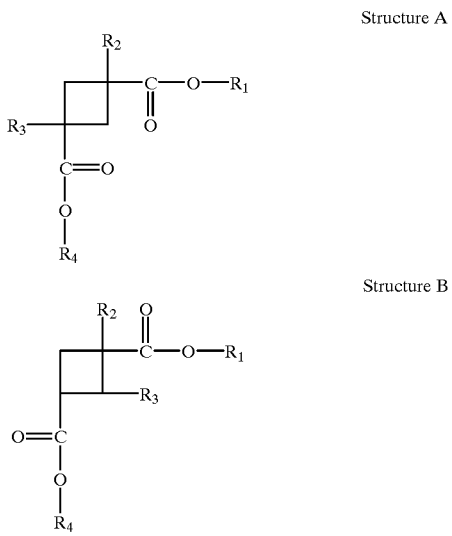

Structure A

Structure B where $R_1$ to $R_4$ are independently hydrophobic alkyl chains. The alkyl cycloalkylacrylate copolymers are soluble in hydrocarbons, such as isododecane, but not in water, thus enhancing the film-forming effect of the copolymer in a volatile solvent base.

When included, the alkyl cycloalkylacrylate copolymer or copolymers can be from about 0.01 percent by weight to about 85 percent by weight. Preferably, this copolymer is about 0.1 percent by weight to about 15 percent by weight of the composition.

The composition may also include other ingredients, such as a volatile solvent, wax, powder, non-volatile oil, and emulsifier.

The volatile solvent of the present invention acts as a carrier for the other components of the cosmetic, rapidly and evenly dispersing them on the skin, and then evaporating. The preferred volatile solvent includes $C_6$ to $C_{20}$ hydrocarbon fractions, more preferably an isoparaffin and most preferably the specific $C_{12}$ fraction isododecane. Alternatively, cyclomethicone, up to a preferred limit of about 30 weight percent, is also favored.

The volatile solvent may be present in an amount from about 0.01 percent by weight to about 85 percent by weight. However, in certain compositions, less volatile solvent than the maximum 85 percent by weight is desired. For example, a foundation preferably contains no more than about 50 percent by weight of volatile solvent. One or more volatile solvents may be present in the above total amount.

The preferred wax or waxes can be of vegetable, synthetic or hydrocarbon origin. The wax preferably should have a melting point in the range between about 35° C. to 120° C.

The wax is present in an amount from about 0.01 percent by weight to about 50 percent by weight of the composition. A greater amount of wax is preferred in an anhydrous blush or lipstick than in a mascara. Therefore, the amount of wax in an anhydrous blush or lipstick is preferably about 0.01 percent by weight to about 50 percent by weight, whereas in a mascara, the amount of wax is preferably about 0.01 to about 25 percent by weight of the composition.

The dry powder, as discussed above, gives color and sheen to the cosmetics of the present composition. The preferred dry powder includes an organic or an inorganic powder or a combination thereof. The dry powder preferably is a certified organic lake, a stain or an inorganic pigment having a particle size between about 0.02 and about 85 microns in diameter. The dry powder or powders component is preferably present in an amount from about 0.1 percent by weight to about 65 percent by weight of the composition, with the higher figure most suitable for such products as lipsticks or foundations. A blush or mascara preferably contains no more than about 20 to 25 weight percent of powder.

It is also preferred, depending on the final product being formulated, to include a nonvolatile oil, emulsifier, water or a combination thereof to the finished cosmetic composition. The copolymers of the present invention are suitable for use in both water-based and anhydrous systems.

A preferred cosmetic composition according to the present invention comprises from about 0.01 weight percent to about 85 weight percent of a block copolymer of styrene, ethylene and propylene type monomers. In a more preferred embodiment, the composition also includes from about 0.01 weight percent to about 85 weight percent of alkyl cycloalkylacrylate copolymer. Another preferred cosmetic composition according to the present invention comprises:

1) from about 0.01 weight percent to about 85 eight percent of a block copolymer of styrene, ethylene and propylene type monomers;
2) from about 0.01 weight percent to about 85 weight percent of alkyl cycloalkylacrylate copolymer;
3) from about 0.01 weight percent to about 85 weight percent volatile solvent;
4) from about 0.01 weight percent to about 50 weight percent wax;
5) from about 0.1 weight percent to about 65 weight percent dry powder; and
6) from about 0.01 weight percent to about 80 weight percent non-volatile oil, emulsifier and/or water.

As discussed above, one or more of each ingredient may be used, but with the total amount of that ingredient set forth above.

Within the preferred ranges set forth above, the following Examples 1 through 3 set forth preferred subset compositions for foundations, blushes or lipsticks, and mascaras, respectively.

EXAMPLE 1

Foundation

|  | Wt. % | |
| --- | --- | --- |
|  | From about | To about |
| Styrene-ethylene/propylene mixed block copolymer | 0.01 | 15 |
| Alkyl cyclomethacrylate copolymer | 0.01 | 15 |

-continued

|  | Wt. % | |
|---|---|---|
|  | From about | To about |
| Volatile Solvent | 0.01 | 50 |
| Wax | 0.01 | 30 |
| Powder | 0.1 | 65 |
| Nonvolatile oil, emulsifier and water | 0.01 | 55 |

EXAMPLE 2

Anhydrous Blush/Lipstick

|  | Wt. % | |
|---|---|---|
|  | From about | To about |
| Styrene-ethylene/propylene mixed block copolymer | 0.01 | 10 |
| Alkyl cyclomethacrylate copolymer | 0.01 | 20 |
| Volatile Solvent | 0.01 | 60 |
| Wax | 0.01 | 50 |
| Powder | 0.1 | 25 |
| Nonvolatile oil and emulsifier | 0.01 | 55 |

EXAMPLE 3

Mascara

|  | Wt. % | |
|---|---|---|
|  | From about | To about |
| Styrene-ethylene/propylene mixed block copolymer | 0.01 | 30 |
| Alkyl cyclomethacrylate copolymer | 0.01 | 50 |
| Volatile Solvent | 0.01 | 70 |
| Wax | 0.01 | 25 |
| Powder | 0.1 | 20 |
| Nonvolatile oil, emulsifier and water | 0.01 | 50 |

The following are illustrative preferred embodiments.

EXAMPLE 4—Pigmented Foundation

| Isododecane | 25.00 |
|---|---|
| Silica-fumed | 0.50 |
| Isooctahexacontane | 1.00 |
| Bentone gel | 3.00 |
| Isododecane/mixed block copolymer | 6.00 |
| Cycloalkylmethacrylate copolymer/isododecane | 2.00 |
| Laurylmethicone copolyol | 2.00 |
| Polyglycerol diisostearate | 0.75 |
| Glyceryl tribehenate | 0.75 |
| Glyceryl rosinate | 4.00 |
| Cosmetic powder | 8.75 |
| Cosmetic pigment | 12.695 |
| Demineralized water | 27.785 |
| Disodium EDTA | 0.20 |
| Sodium hexametaphosphate | 0.15 |

-continued

| Sodium chloride | 0.50 |
|---|---|
| Butylene glycol | 4.00 |
| Methylparaben | 0.40 |
| Xanthan gum | 0.01 |
| Imidazolidinyl urea | 0.50 |

EXAMPLE 5—Waterproof Mascara

| Odorless Mineral Spirits | 32.35 |
|---|---|
| Isododecane/Mixed Block Copolymer | 15.00 |
| Cycloalkylmethacrylate copolymer/isododecane | 4.00 |
| Pentaerythritol rosinate | 2.50 |
| Iron oxide | 5.00 |
| Cosmetic wax | 9.30 |
| Cosmetic powder | 13.00 |
| Hydroxylated lanolin | 1.30 |
| Glyceryl Pyroglutamate Monooleate | 0.50 |
| Polybutene | 0.10 |
| Butylated hydroxytoluene | 0.02 |
| Propylparaben | 0.25 |
| Demineralized water | 14.88 |
| Polyvinylpyrrolidone | 0.10 |
| Tetrasodium EDTA | 0.20 |
| Acetylated POE lanolin alcohol | 0.20 |
| Propylene glycol | 1.00 |
| Methylparaben | 0.30 |
| 2-phenoxyethanol | 0.50 |

EXAMPLE 6—Blush

| Tridecyl trimellitate | 14.68 |
|---|---|
| Isododecane/mixed block copolymer | 4.95 |
| Isododecane | 7.35 |
| Cyclomethicone | 4.50 |
| Cycloalkylmethacrylate copolymer/isododecane | 20.00 |
| Pentaerythritol rosinate | 1.20 |
| Isopropyl lanolate | 5.00 |
| Cosmetic wax | 22.00 |
| BHT | 0.02 |
| Ethylhexyl palmitate | 5.00 |
| Jojoba oil | 0.50 |
| Ethylhexyl methoxycinnamate | 1.00 |
| Tocopherol acetate | 0.05 |
| Organic pigment lake | 0.55 |
| Iron oxide | 1.35 |
| Titanium dioxide | 3.85 |
| Mica | 8.00 |

EXAMPLE 7—Lip Color

| Cosmetic wax | 14.60 |
|---|---|
| Diisostearyl fumarate | 9.80 |
| Stearyl dimethicone | 3.90 |
| Ethylhexyl methoxycinnamate | 3.20 |
| Benzophenone 3 | 1.50 |
| Iron oxide pigment | 9.60 |
| Cosmetic powder | 2.84 |
| Cyclomethicone | 45.05 |
| Isododecane | 6.00 |

| | -continued | |
|---|---|---|
| Isododecane/mixed block copolymer | | 2.00 |
| Squalane | | 1.50 |
| Cycloalkylmethacrylate copolymer/isododecane | | 0.01 |

The invention having been thus described with particular reference to the preferred forms thereof, it will be obvious that various changes and modifications may be made therein without departing from the spirit and scope of the invention as defined in the appended claims.

What we claim is:

1. A wear-resistant cosmetic composition comprising a styrene-ethylene/propylene block copolymer and an alkyl cycloalkylacrylate copolymer in a cosmetically acceptable carrier, wherein said alkyl cycloalkylacrylate copolymer is of a structure selected from the group consisting of Structure A, Structure B, an isomer of Structure A, an isomer of Structure B, and a combination thereof:

Structure A

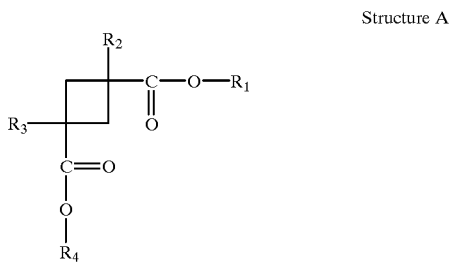

Structure B

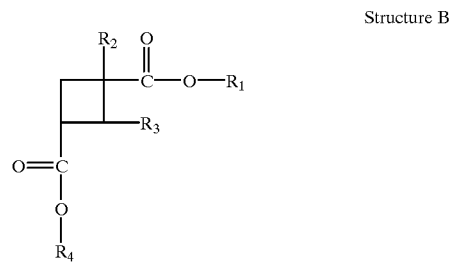

where $R_1$ to $R_4$ are hydrogen or hydrophobic alkyl chains.

2. The cosmetic composition of claim 1, wherein said styrene-ethylene/propylene block copolymer is of a structure as follows:

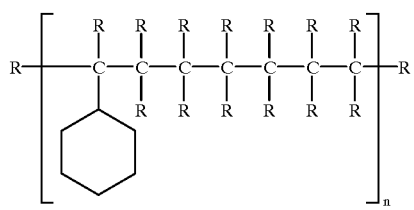

wherein $n \geq 1$ and R represents a hydrogen or a hydrophobic alkyl group.

3. The cosmetic composition of claim 1, wherein said styrene-ethylene/propylene block copolymer is present from about 0.01 percent by weight to about 85 percent by weight of a total composition weight.

4. The cosmetic composition of claim 1, wherein said styrene-ethylene/propylene block copolymer is present from about 0.1 weight percent to about 15 percent by weight of a total composition weight.

5. The cosmetic composition of claim 1, further comprising: about 0.1 weight percent to about 65 weight percent dry powder.

6. The cosmetic composition of claim 1, wherein said alkyl cycloalkylacrylate copolymer is present at from about 0.01 weight percent to about 85 weight percent.

7. The cosmetic composition of claim 1, wherein said alkyl cycloalkylacrylate copolymer is present at from about 0.1 weight percent to about 15 weight percent.

8. The cosmetic composition of claim 1, wherein said carrier comprises a volatile solvent.

9. The cosmetic composition of claim 9, wherein said volatile solvent is present at from about 0.01 weight percent to about 85 weight percent.

10. The cosmetic composition of claim 9, wherein said volatile solvent comprises a volatile hydrocarbon.

11. The cosmetic composition of claim 9, wherein said volatile solvent is silicon-based.

12. The cosmetic composition of claim 1, wherein said carrier comprises a volatile hydrocarbon.

13. The cosmetic composition of claim 1, wherein said carrier comprises silicone.

14. The cosmetic composition of claim 1, further comprising from about 0.01 weight percent to about 50 weight percent wax.

15. The cosmetic composition of claim 1, wherein said carrier comprises water.

16. The cosmetic composition of claim 1, further comprising a non-volatile oil.

17. The cosmetic composition of claim 1, further comprising an emulsifier.

18. A wear resistant cosmetic composition comprising:
from about 0.01 to about 30 percent by weight styrene-ethylene/propylene block copolymer;
from about 0.01 to about 50 percent by weight alkyl cycloalkylacrylate copolymer, wherein said alkyl cycloalkylacrylate copolymer is of a structure selected from the group consisting of Structure A, Structure B, an isomer of Structure A, an isomer of Structure B, and a combination thereof:

Structure A

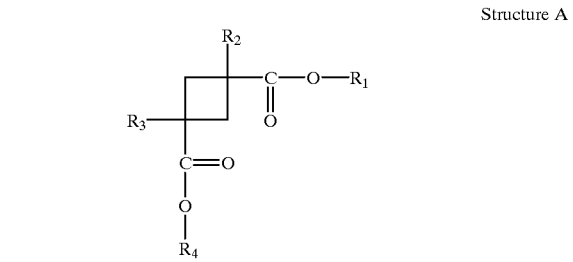

Structure B

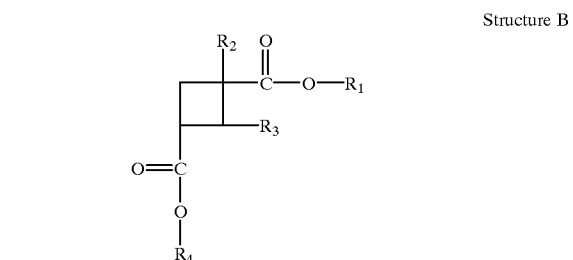

where $R_1$ to $R_4$ are hydrogen or hydrophobic alkyl chains;
from about 0.01 to about 70 percent by weight volatile solvent;
from about 0.01 to about 50 percent by weight wax; and
from about 0.1 to about 65 percent powders.

* * * * *

UNITED STATES PATENT AND TRADEMARK OFFICE
CERTIFICATE OF CORRECTION

PATENT NO. : 6,083,516
DATED : July 4, 2000
INVENTOR(S) : Curtis et al.

It is certified that error appears in the above-identified patent and that said Letters Patent is hereby corrected as shown below:

At claim 9, line 1, "of claim 9" should read --of claim 8--.

At claim 10, line 1, "of claim 9" should read --of claim 8--.

At claim 11, line 1, "of claim 9" should read --of claim 8--.

Signed and Sealed this

Twenty-second Day of May, 2001

*Attest:*

NICHOLAS P. GODICI

*Attesting Officer*  *Acting Director of the United States Patent and Trademark Office*